(12) United States Patent
Saiki et al.

(10) Patent No.: US 10,059,829 B2
(45) Date of Patent: Aug. 28, 2018

(54) RUBBER COMPOSITION, TIRE, AMINE COMPOUND, AND ANTI-AGING AGENT

(71) Applicant: OTSUKA CHEMICAL CO., LTD., Osaka-shi, Osaka (JP)

(72) Inventors: Aya Saiki, Kunitachi (JP); Hidehiro Minashima, Kodaira (JP); Yuzaburo Yano, Kodaira (JP); Noriaki Shiina, Osaka (JP); Kazuhiro Kodama, Osaka (JP); Mifuyu Ueno, Osaka (JP); Takashi Sato, Osaka (JP); Shinya Nakashima, Osaka (JP); Masaki Abe, Osaka (JP)

(73) Assignee: OTSUKA CHEMICAL CO., LTD., Osaka-shi, Osaka (JP)

( * ) Notice: Subject to any disclaimer, the term of this patent is extended or adjusted under 35 U.S.C. 154(b) by 0 days.

(21) Appl. No.: 15/312,785

(22) PCT Filed: May 22, 2015

(86) PCT No.: PCT/JP2015/002597
§ 371 (c)(1),
(2) Date: Nov. 21, 2016

(87) PCT Pub. No.: WO2015/178038
PCT Pub. Date: Nov. 26, 2015

(65) Prior Publication Data
US 2017/0166727 A1   Jun. 15, 2017

(30) Foreign Application Priority Data

May 22, 2014  (JP) .................... 2014-106395

(51) Int. Cl.
| C07C 211/55 | (2006.01) |
| C08K 5/18 | (2006.01) |
| C07C 211/53 | (2006.01) |
| C08L 7/00 | (2006.01) |
| C08L 9/00 | (2006.01) |

(52) U.S. Cl.
CPC .............. *C08K 5/18* (2013.01); *C07C 211/53* (2013.01); *C07C 211/55* (2013.01); *C08L 7/00* (2013.01); *C08L 9/00* (2013.01); *C08L 2201/08* (2013.01)

(58) Field of Classification Search
CPC ........ C08K 5/18; C07C 211/53; C07C 211/55
See application file for complete search history.

(56) References Cited

U.S. PATENT DOCUMENTS

| 2,705,224 A | * | 3/1955 | Hill ........................... C08K 5/18 524/255 |
| 2,939,861 A | * | 6/1960 | Ambelang ................ C08K 5/18 523/315 |
| 2,939,867 A | | 6/1960 | Ambelang |
| 3,277,174 A | | 10/1966 | Wheeler |
| 3,975,414 A | | 8/1976 | Kline |
| 4,376,846 A | | 3/1983 | Kotani et al. |
| 2005/0051248 A1 | | 3/2005 | Hotaka et al. |
| 2009/0165919 A1 | | 7/2009 | Araujo Da Silva et al. |

FOREIGN PATENT DOCUMENTS

| CN | 103059355 A | 4/2013 |
| EP | 2604650 A1 | 6/2013 |
| JP | H0892370 A | 4/1996 |
| JP | 2005232355 A | 9/2005 |
| JP | 2010509415 A | 3/2010 |
| JP | 2010536952 A | 12/2010 |
| JP | 2013155259 A | 8/2013 |
| KR | 20020089891 A | 11/2002 |
| KR | 101392733 B1 | 5/2014 |

OTHER PUBLICATIONS

Aug. 22, 2017, Notification of Reasons for Refusal issued by the Japan Patent Office in the corresponding Japanese Patent Application No. 2014-106395.
Chemical Library, Florida Center for Heterocyclic Compounds, Department of Chemistry, University of Florida, CAS Registry No. 865078-88-2, 2005, Retrieved from: STN, United States of America.
A. E. Oberster et al., Syntheses of novel substituted p-phenylenediamines, Canadian Journal of Chemistry, Feb. 1, 1967, vol. 45, No. 3, p. 195-201.
Jun. 30, 2015, International Search Report issued in the International Patent Application No. PCT/JP2015/002597.
Nov. 22, 2016, International Preliminary Report on Patentability issued in the International Patent Application No. PCT/JP2015/002597.
Friedrich Klages et al., "The anomalous osmotic behavior of chain molecules. V. synthesis and cryoscopy of additional compounds with beaded-chain-molecule-structure", Chemische Berichte, Oct. 1948, pp. 400-410, 81, Germany.
Dec. 4, 2017, Extended European Search Report issued by the European Patent Office in the corresponding European Patent Application No. 15795903.2.
Nov. 13, 2017, Office Action issued by the State Intellectual Property Office in the corresponding Chinese Patent Application No. 201580025825.1.
Jun. 7, 2018, Office Action issued by the State Intellectual Property Office in the corresponding Chinese Patent Application No. 201580025825.1.

* cited by examiner

*Primary Examiner* — Vickey Nerangis
(74) *Attorney, Agent, or Firm* — Kenja IP Law PC

(57) ABSTRACT

Provided is a rubber composition that has better weather resistance than conventional rubber compositions and can inhibit surface discoloration of a rubber article. The rubber composition contains at least one rubber component selected from natural rubber and diene-based synthetic rubbers and, blended therewith, at least one amine compound represented by formula (I) shown below. In formula (I), $R^1$ and $R^2$ each represent, independently of one another, an alkyl group having a carbon number of 1-10, an aralkyl group, or a phenyl group, and A represents an alkylene group having a carbon number of 6-30 that may include an interposed phenylene group.

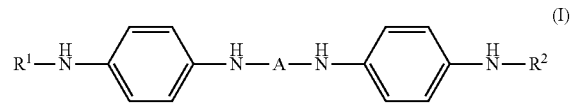

(I)

6 Claims, No Drawings

RUBBER COMPOSITION, TIRE, AMINE COMPOUND, AND ANTI-AGING AGENT

TECHNICAL FIELD

The present disclosure relates to a rubber composition, a tire, an amine compound, and an anti-aging agent, and, in particular, relates to a rubber composition that is suitable for use in tread rubber or sidewall rubber of a tire.

BACKGROUND

Rubber articles having natural rubber or a diene-based synthetic rubber as a raw material generally deteriorate over time and suffer from crack formation at the surface thereof when exposed to an environment in which ozone is present. Such cracks propagate as the rubber article is subjected to static stress and dynamic stress, and may eventually result in rupturing of the rubber article.

In order to prevent and inhibit the formation and propagation of cracks in a rubber article due to ozone, particularly in the case of tread rubber or sidewall rubber of a tire, it has become common practice to use a rubber composition that contains an anti-aging agent such as N-(1,3-dimethylbutyl)-N'-phenyl-p-phenylenediamine (PTL 1 and 2).

CITATION LIST

Patent Literature

PTL 1: JP 2010-509415 A
PTL 2: JP 2010-536952 A

SUMMARY

Technical Problem

However, when an anti-aging agent such as described above is used in a rubber article, the external appearance of the rubber article may deteriorate as a consequence of the anti-aging agent having a high tendency to migrate to the surface of the rubber over time, leading to discoloration and staining of the rubber surface by what is referred to as "blooming".

In recent years, there has been demand for improvement of rubber article weather resistance, such as ozone resistance. Particularly in the case of tire production, strategies are being adopted for reducing the gauge thickness of various tire members in order to provide better fuel efficiency and conserve resources. Under these circumstances, there is demand for a rubber composition that has even better weather resistance than a conventional rubber composition containing an anti-aging agent such as described above.

Therefore, one objective of the present disclosure is to provide a rubber composition that has better weather resistance than conventional rubber compositions and can inhibit surface discoloration of a rubber article. Another objective of the present disclosure is to provide a tire that has superior weather resistance and in which rubber article surface discoloration is inhibited.

Solution to Problem

The inventors conducted diligent investigation in order to achieve the objectives described above, resulting in the discovery that a rubber composition that has superior weather resistance and that can inhibit surface discoloration of a rubber article can be obtained through blending of a compound having a specific structure with a rubber component. This discovery led to the present disclosure.

Specifically, a presently disclosed rubber composition comprises at least one rubber component selected from natural rubber and diene-based synthetic rubbers and, blended therewith, at least one amine compound represented by formula (I) shown below $$R^1-\underset{H}{N}-\underset{}{\underset{}{\bigcirc}}-\underset{H}{N}-A-\underset{H}{N}-\underset{}{\underset{}{\bigcirc}}-\underset{H}{N}-R^2 \quad (I)$$

where, in formula (I), $R^1$ and $R^2$ each represent, independently of one another, an alkyl group having a carbon number of 1-10, an aralkyl group, or a phenyl group, and A represents an alkylene group having a carbon number of 6-30 that may include an interposed phenylene group. As a result of the presently disclosed rubber composition containing the aforementioned amine compound as an anti-aging agent, weather resistance of the presently disclosed rubber composition can be significantly improved compared to conventional rubber compositions and surface discoloration of a rubber article can be inhibited.

From a viewpoint of sufficiently improving weather resistance and preventing discoloration, it is preferable that the amine compound contained in the presently disclosed rubber composition is represented by formula (II) shown below $$R^1-\underset{H}{N}-\underset{}{\underset{}{\bigcirc}}-\underset{H}{N}-\underset{\underset{CH_3}{|}}{CH}-(CH_2)_m-\underset{\underset{CH_3}{|}}{CH}-\underset{H}{N}-\underset{}{\underset{}{\bigcirc}}-\underset{H}{N}-R^2 \quad (II)$$

where, in formula (II), $R^1$ and $R^2$ each represent a phenyl group and m represents an integer of 8-16.

In the presently disclosed rubber composition, a blending amount of the amine compound is preferably in a range of from 0.2 parts by mass to 10 parts by mass relative to 100 parts by mass of the rubber component. As a result of the blending amount of the amine compound being in the range described above, it is possible to sufficiently improve weather resistance and inhibit discoloration while also restricting the amount of the amine compound that is consumed.

A presently disclosed tire comprises a tire member in which the above-described rubber composition is used. The aforementioned tire member is preferably either or both of a tread and a sidewall. The presently disclosed tire has superior weather resistance and rubber article surface discoloration is inhibited therein.

A presently disclosed amine compound is represented by formula (I) shown below $$R^1-\underset{H}{N}-\underset{}{\underset{}{\bigcirc}}-\underset{H}{N}-A-\underset{H}{N}-\underset{}{\underset{}{\bigcirc}}-\underset{H}{N}-R^2 \quad (I)$$

where, in formula (I), $R^1$ and $R^2$ each represent, independently of one another, an alkyl group having a carbon number of 1-10, an aralkyl group, or a phenyl group, and A represents an alkylene group having a carbon number of 6-30 that may include an interposed phenylene group. A presently disclosed anti-aging agent for natural rubber and diene-based synthetic rubber-use comprises the above-described amine compound.

Advantageous Effect

According to the present disclosure, it is possible to provide a rubber composition that has better weather resistance than conventional rubber compositions and that can inhibit surface discoloration of a rubber article, and also to provide a tire that has superior weather resistance and in which rubber article surface discoloration is inhibited.

DETAILED DESCRIPTION

<Rubber Composition>
The following provides a detailed description of the present disclosure. A presently disclosed rubber composition contains at least one rubber component selected from natural rubber and diene-based synthetic rubbers and, blended therewith, at least one amine compound represented by formula (I) shown above.
<<Rubber Component>>
Examples of rubber components that can be used in the presently disclosed rubber composition include natural rubber (NR) and diene-based synthetic rubbers such as isoprene rubber (IR), butadiene rubber (BR), and styrene-butadiene copolymer rubber (SBR). One of these rubber components may be used individually, or two or more of these rubber components may be used in combination as necessary.
<<Amine Compound>>
The presently disclosed rubber composition contains at least one amine compound represented by formula (I) shown above. In formula (I), $R^1$ and $R^2$ each represent, independently of one another, an alkyl group having a carbon number of 1-10, an aralkyl group, or a phenyl group, and A represents an alkylene group having a carbon number of 6-30 that may include an interposed phenylene group.

The amine compound represented by formula (I) that is used in the presently disclosed rubber composition has a high molecular weight compared to conventional anti-aging agents and, as shown in formula (I), includes a bridge moiety having a characteristic and comparatively long chain length section. Specifically, the amine compound represented by formula (I) includes a moiety composed by —NH-A-NH—. It is thought that as a result of the amine compound having a high molecular weight and including this characteristic bridge moiety, the rate of diffusion of the amine compound within the rubber composition is reduced and, accordingly, migration of the amine compound to the rubber surface is inhibited to a greater extent. Furthermore, in the amine compound, two nitrogen atoms that are present at opposite ends of A in formula (I) are each bonded to one hydrogen atom (i.e., forming what is referred to as a "secondary amino group"). It is thought that the presence of these bonds in the structure represented by formula (I) contributes to the characteristic effect of improved weather resistance.

The amine compound represented by formula (I) has an excellent anti-aging effect with respect to rubber components such as natural rubber and diene-based synthetic rubbers, and can be used as an anti-aging agent for rubber component-use.

The following provides a description of the various chemical groups referred to in the present specification.

Examples of alkyl groups having a carbon number of 1-4 include linear and branched alkyl groups having a carbon number of 1-4 such as a methyl group, an ethyl group, an n-propyl group, an isopropyl group, an n-butyl group, an isobutyl group, a sec-butyl group, and a tert-butyl group.

Examples of alkyl groups having a carbon number of 1-10 include the examples of alkyl groups having a carbon number of 1-4 provided above and other linear and branched alkyl groups having a carbon number of 1-10 such as various pentyl groups, examples of which include an n-pentyl group, an isopentyl group, a neopentyl group, and a tert-pentyl group; various hexyl groups, examples of which include an n-hexyl group, an isohexyl group, and a 4-methyl-2-pentyl group; various heptyl groups, examples of which include an n-heptyl group and a 4-heptyl group; various octyl groups, examples of which include an n-octyl group, an isooctyl group, and a 2-ethylhexyl group; various nonyl groups, examples of which include an n-nonyl group, a 3-ethylheptyl group, and a 4-methyloctyl group; and various decyl groups, examples of which include an n-decyl group and a 4-ethyloctyl group.

Examples of aralkyl groups include a benzyl group and a phenethyl group.

Examples of alkylene groups having a carbon number of 6-30 include linear and branched alkylene groups having a carbon number of 6-30 such as a hexamethylene group, a 1,4-dimethyltetramethylene group, a heptamethylene group, an octamethylene group, a nonamethylene group, a decamethylene group, a 1,8-dimethyloctamethylene group, a dodecamethylene group, a 1,10-dimethyldecamethylene group, a tetradecamethylene group, a 1,12 dimethylundecamethylene group, a hexadecamethylene group, a 1,14-dimethyltetradecamethylene group, a 1,12-diethylundecamethylene group, an octadecamethylene group, a 1,16-dimethyloctadecamethylene group, an icosamethylene group, a henicosamethylene group, a docosamethylene group, and a triacontamethylene group. The alkylene group having a carbon number of 6-30 that is represented by A in formula (I) may include an interposed phenylene group. Examples of such alkylene groups include:

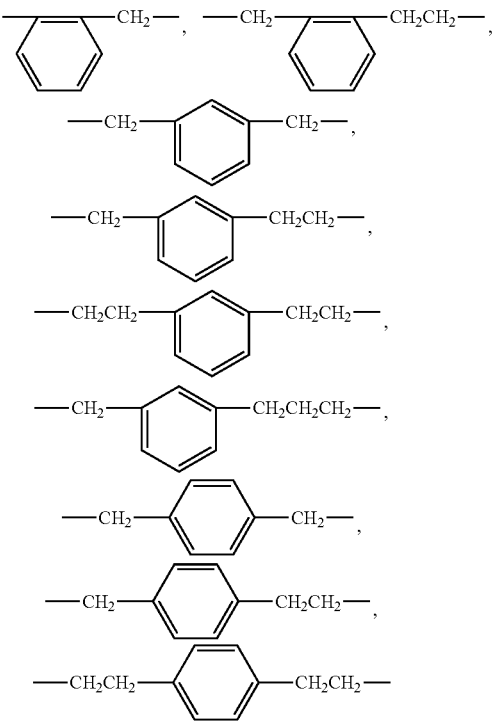

In the amine compound represented by formula (I), $R^1$ and $R^2$ are each, independently of one another, an alkyl group having a carbon number of 1-10, an aralkyl group, or a phenyl group. However, from a viewpoint of sufficiently improving weather resistance and preventing discoloration, it is preferable that $R^1$ and $R^2$ are each a branched alkyl group having a carbon number of 5-8, an aralkyl group, or a phenyl group, and more preferable that $R^1$ and $R^2$ are each a phenyl group.

In the amine compound represented by formula (I), A is an alkylene group having a carbon number of 6-30 that may include an interposed phenylene group. However, from a viewpoint of sufficiently improving weather resistance and preventing discoloration, it is preferable that A is a linear or branched alkylene group having a carbon number of 8-24, more preferable that A is a linear or branched alkylene group having a carbon number of 10-22, further preferable that A is an alkylene group represented by formula (B) shown below

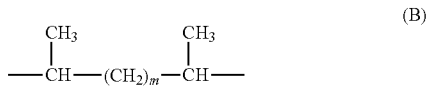

(B)

that has a carbon number of 12-20 (i.e., in formula (B), m is an integer of 8-16), and particularly preferable that A is an alkylene group represented by formula (B) shown above that has a carbon number of 14-18 (i.e., in formula (B), m is an integer of 10-14).

In other words, the amine compound used in the presently disclosed rubber composition is more preferably a compound represented by formula (II) shown below

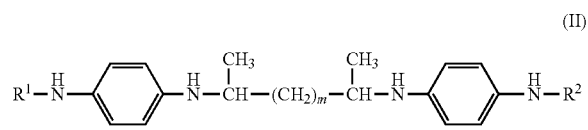

(II)

(in formula (II), $R^1$ and $R^2$ are the same as previously described) for which m is an integer of 8-16, and is particularly preferably a compound represented by formula (II) shown above for which m is an integer of 10-14.

Moreover, in the compound represented by formula (II), $R^1$ and $R^2$ are preferably each a branched alkyl group having a carbon number of 5-8, an aralkyl group, or a phenyl group, and are more preferably each a phenyl group.

Examples of compounds such as described above include N,N'-bis[4-(isopropylamino)phenyl]hexane-1,6-diamine, N,N'-bis(4-anilinophenyl)hexane-1,6-diamine, N,N'-bis[4-(4-methylpentan-2-ylamino)phenyl]decane-1,10-diamine, N,N'-bis[4-(heptan-4-ylamino)phenyl]decane-1,10-diamine, N,N'-bis(4-benzylaminophenyl)decane-1,10-diamine, N,N'-bis(4-anilinophenyl)decane-1,10-diamine, N,N'-bis(4-anilinophenyl)dodecane-2,11-diamine, N,N'-bis(4-anilinophenyl)hexadecane-2,15-diamine, N,N'-bis(4-anilinophenyl)tetradecane-2,13-diamine, N,N'-bis(4-anilinophenyl)octadecane-2,17-diamine, N,N'-bis(4-anilinophenyl)icosane-1,20-diamine, N,N'-bis[4-(isobutylamino)phenyl]benzene-1,3-dimethaneamine, N,N'-bis[4-(sec-butylamino)phenyl]benzene-1,3-dimethaneamine, N,N'-bis[4-(isobutylamino)phenyl]benzene-1,4-dimethaneamine, and N,N'-bis[4-(sec-butylamino)phenyl]benzene-1,4-dimethaneamine. Of these compounds, N,N'-bis[4-(4-methylpentan-2-ylamino)phenyl]decane-1,10-diamine, N,N'-bis[4-(heptan-4-ylamino)phenyl]decane-1,10-diamine, N,N'-bis(4-anilinophenyl)dodecane-2,11-diamine, N,N'-bis(4-anilinophenyl)hexadecane-2,15-diamine, N,N'-bis(4-anilinophenyl)tetradecane-2,13-diamine, and N,N'-bis(4-anilinophenyl)octadecane-2,17-diamine are preferable.

The amine compound represented by formula (I) can be produced by a reaction shown below in reaction formula 1.

(Reaction formula 1)

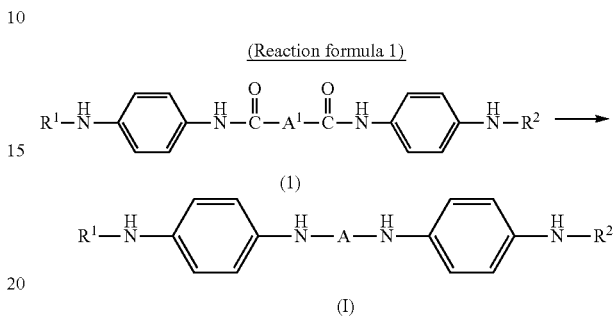

(In reaction formula 1, $R^1$, $R^2$, and A are the same as previously described and $A^1$ is an alkylene group having a carbon number of 2-28.)

According to reaction formula 1, the amine compound represented by formula (I) can be produced by reducing amide carbonyl bonds of a diamide compound represented by formula (1) in a solvent through the action of a reducing agent or through catalytic hydrogen reduction using a metal catalyst.

In a reaction in which a reducing agent is used in reaction formula 1, the solvent that is used can be selected from a wide range of commonly known solvents that are inert with respect to the reaction. Examples of solvents that can be used include ether solvents such as dimethyl ether, diethyl ether, diisopropyl ether, tert-butyl methyl ether, tetrahydrofuran, dioxane, tetrahydropyran, and 1,2-dimethoxyethane; halogen-containing solvents such as dichloromethane and carbon tetrachloride; and, in the case of a borohydride reducing agent, alcohol solvents such as methanol, ethanol, n-propanol, isopropyl alcohol, and n-butanol. One of these solvents may be used individually, or a mixture of two or more of these solvents may be used as necessary.

The amount of such solvents that is used relative to 1 part by mass of the diamide compound represented by formula (1) is normally approximately 1 part by mass to 500 parts by mass and preferably approximately 1 part by mass to 20 parts by mass.

Examples of reducing agents that can be used in the reaction in reaction formula 1 include lithium aluminum hydride, sodium borohydride, borane, and diborane. Furthermore, lithium aluminum hydride may be used in combination with aluminum chloride, or sodium borohydride may be used in combination with a Lewis acid such as tin tetrachloride or boron trifluoride diethyl ether complex.

The amount of such reducing agents that is used relative to the diamide compound represented by formula (1) is normally from 1.5 equivalents to 20.0 equivalents, preferably from 1.5 equivalents to 6.0 equivalents, and more preferably 1.5 equivalents.

In a catalytic hydrogen reduction reaction in reaction formula 1, the solvent that is used can be selected from a wide range of commonly known solvents that are inert with respect to the reaction. Examples of solvents that can be used include alcohol solvents such as methanol, ethanol, n-propanol, isopropyl alcohol, and n-butanol; organic acids such as acetic acid and propionic acid; hydrocarbon solvents such as cyclohexane; and ether solvents such as tetrahydrofuran. One of these solvents may be used individually, or a mixture of two or more of these solvents may be used as necessary.

The amount of such solvents that is used relative to 1 part by mass of the diamide compound represented by formula (1) is normally approximately 1 part by mass to 500 parts by mass and preferably approximately 1 part by mass to 20 parts by mass.

Examples of metal catalysts that can be used in the catalytic hydrogen reduction reaction in reaction formula 1 include palladium on carbon, platinum black (platinum on carbon), copper oxide/zinc oxide/aluminum oxide mixtures, copper oxide/chromium oxide/manganese trioxide/barium oxide mixtures, copper oxide/zinc oxide mixtures, Raney nickel, and Raney cobalt.

The amount of such metal catalysts that is used relative to the diamide compound represented by formula (1) is normally from 0.0001 parts by mass to 0.5 parts by mass, preferably from 0.0001 parts by mass to 0.1 parts by mass, and more preferably from 0.0001 parts by mass to 0.01 parts by mass.

The reaction can normally be carried out in a temperature range of from −78° C. to the boiling temperature of the solvent that is used. However, the reaction is normally carried out at approximately −10° C. to 50° C. and preferably at around room temperature.

Although it is not possible to make generalizations about the reaction time since the reaction time varies depending on the reaction temperature and so forth, the reaction is normally completed in approximately 0.5 hours to 24 hours.

The reaction is carried out under a hydrogen atmosphere at a pressure that is normally from atmospheric pressure to 10 MPa, preferably from atmospheric pressure to 1.0 MPa, and more preferably around atmospheric pressure.

Alternatively, the amine compound represented by formula (I) can be produced by a reaction shown below in reaction formula 2.

(Reaction formula 2)

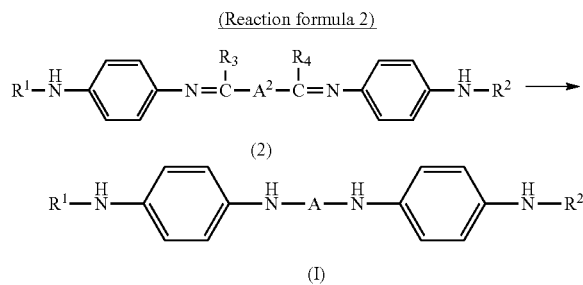

(In reaction formula 2, $R^1$, $R^2$, and A are the same as previously described, $R^3$ and $R^4$ each represent a hydrogen atom or an alkyl group having a carbon number of 1-4, and may be the same or different, $A^2$ represents an alkylene group having a carbon number of 2-28, and a total carbon number of $R^3$, $R^4$, and $A^2$ is no greater than 28.)

According to reaction formula 2, the compound represented by formula (I) can be produced by reducing imino bonds of a diimino compound represented by formula (2) in a solvent through the action of a reducing agent or through catalytic hydrogen reduction using a metal catalyst.

In a reaction in which a reducing agent is used in reaction formula 2, the solvent that is used can be selected from a wide range of commonly known solvents that are inert with respect to the reaction. Examples of solvents that can be used include ether solvents such as dimethyl ether, diethyl ether, diisopropyl ether, tert-butyl methyl ether, tetrahydrofuran, dioxane, tetrahydropyran, and 1,2-dimethoxyethane; halogen-containing solvents such as dichloromethane and carbon tetrachloride; and, in the case of a borohydride reducing agent, alcohol solvents such as methanol, ethanol, n-propanol, isopropyl alcohol, and n-butanol. One of these solvents may be used individually, or a mixture of two or more of these solvents may be used as necessary.

The amount of such solvents that is used relative to 1 part by mass of the diimino compound represented by formula (2) is normally approximately 1 part by mass to 500 parts by mass and preferably approximately 5 parts by mass to 100 parts by mass.

Examples of reducing agents that can be used in the reaction in reaction formula 2 include lithium aluminum hydride, sodium borohydride, lithium borohydride, sodium cyanoborohydride, and lithium triethylborohydride.

The amount of such reducing agents that is used relative to the diimino compound represented by formula (2) is normally from 0.5 equivalents to 10.0 equivalents, preferably from 0.5 equivalents to 2.0 equivalents, and more preferably from 0.5 equivalents to 1.0 equivalents.

In a catalytic hydrogen reduction reaction in reaction formula 2, the solvent that is used can be selected from a wide range of commonly known solvents that are inert with respect to the reaction. Examples of solvents that can be used include alcohol solvents such as methanol, ethanol, n-propanol, isopropyl alcohol, and n-butanol; organic acids such as acetic acid and propionic acid; hydrocarbon solvents such as cyclohexane; and ether solvents such as tetrahydrofuran. One of these solvents may be used individually, or a mixture of two or more of these solvents may be used as necessary.

The amount of such solvents that is used relative to 1 part by mass of the diimino compound represented by formula (2) is normally approximately 1 part by mass to 500 parts by mass and preferably approximately 1 part by mass to 20 parts by mass.

Examples of metal catalysts that can be used in the catalytic hydrogen reduction reaction in reaction formula 2 include palladium on carbon, platinum black (platinum on carbon), sulfided platinum on carbon, platinum oxide, Raney nickel, and Raney cobalt.

The amount of such metal catalysts that is used relative to the diimino compound represented by formula (2) is normally from 0.0001 parts by mass to 0.5 parts by mass, preferably from 0.0001 parts by mass to 0.1 parts by mass, and more preferably from 0.0001 parts by mass to 0.01 parts by mass.

The reaction can normally be carried out in a temperature range of from −78° C. to the boiling temperature of the solvent that is used. However, the reaction is normally carried out at approximately −10° C. to 50° C. and preferably at around room temperature.

Although it is not possible to make generalizations about the reaction time since the reaction time varies depending on the reaction temperature and so forth, the reaction is normally completed in approximately 0.5 hours to 24 hours.

The reaction is carried out under a hydrogen atmosphere at a pressure that is normally from atmospheric pressure to 10 MPa, preferably from atmospheric pressure to 1.0 MPa, and more preferably around atmospheric pressure.

The diamide compound represented by formula (1) can be produced by a method such as shown below in reaction formula 3.

(Reaction formula 3)

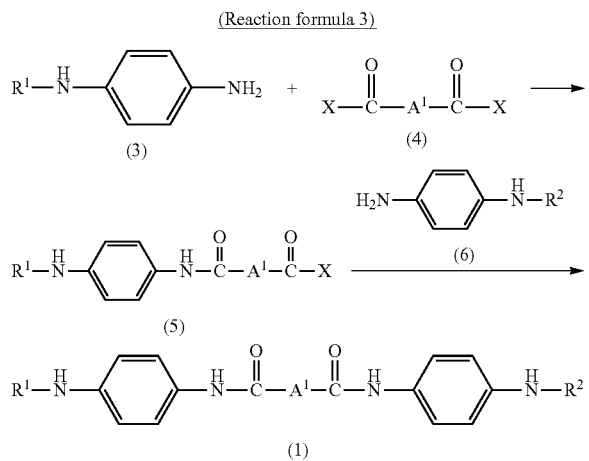

(In reaction formula 3, $R^1$, $R^2$, and $A^1$ are the same as previously described, and X represents a halogen atom or an alkoxy group having a carbon number of 1-4.)

According to reaction formula 3, the diamide compound represented by formula (1) can be produced by causing an acid derivative represented by formula (4) to act on an aniline compound represented by formula (3) to produce an amide compound represented by formula (5) and subsequently causing an aniline compound represented by formula (6) to act on the amide compound represented by formula (5) in the same way.

Amidation in each of these reactions can be carried out by adopting a commonly known reaction for producing an amide through the reaction of an amine with a carboxylic acid ester or an acid halide.

Note that in a situation in which the substituents $R^1$ and $R^2$ are the same, the diamide compound represented by formula (1) can be produced through a single-step reaction in which at least 2 equivalents of the aniline compound represented by formula (3) is used relative to the acid derivative represented by formula (4).

The diimino compound represented by formula (2) can be produced by a method such as shown below in reaction formula 4.

(Reaction formula 4)

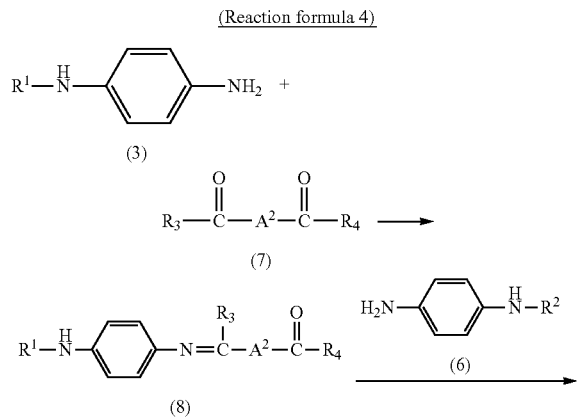

-continued

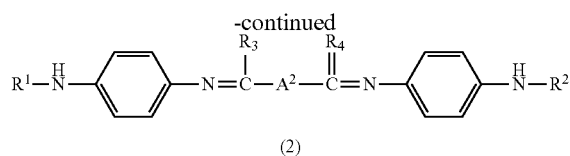

(In reaction formula 4, $R^1$, $R^2$, $R^3$, $R^4$, and $A^2$ are the same as previously described.)

According to reaction formula 4, the diimino compound represented by formula (2) can be produced by causing a dicarbonyl compound represented by formula (7) to act on the aniline compound represented by formula (3) to produce an imino compound represented by formula (8) and subsequently causing the aniline compound represented by formula (6) to act on the imino compound represented by formula (8) in the same way.

Imination in each of these reactions can be carried out by adopting a commonly known reaction for producing an imine from an amine and a carbonyl.

Note that in a situation in which the substituents $R^1$ and $R^2$ are the same, the diimino compound represented by formula (2) can be produced through a single-step reaction in which at least 2 equivalents of the aniline compound represented by formula (3) is used relative to the dicarbonyl compound represented by formula (7).

Furthermore, the amine compound represented by formula (I) can be directly produced by carrying out a reductive amination reaction in which at least 2 equivalents of the aniline compound represented by formula (3) is caused to act on the dicarbonyl compound represented by formula (7) in the presence of a reducing agent or through a catalytic hydrogen reduction reaction in the presence of a metal catalyst.

In a reductive amination reaction using a reducing agent, the solvent that is used can be selected from a wide range of commonly known solvents that are inert with respect to the reaction. Examples of solvents that can be used include ether solvents such as dimethyl ether, diethyl ether, diisopropyl ether, tert-butyl methyl ether, tetrahydrofuran, dioxane, tetrahydropyran, and 1,2-dimethoxyethane; halogen-containing solvents such as dichloromethane and carbon tetrachloride; and, particularly in the case of a borohydride reducing agent, alcohol solvents such as methanol, ethanol, n-propanol, isopropyl alcohol, and n-butanol. One of these solvents may be used individually, or a mixture of two or more of these solvents may be used as necessary.

The amount of such solvents that is used relative to 1 part by mass of the dicarbonyl compound represented by formula (7) is normally approximately 1 part by mass to 500 parts by mass and preferably approximately 5 parts by mass to 100 parts by mass.

Examples of reducing agents that can be used include lithium aluminum hydride, sodium borohydride, lithium borohydride, sodium cyanoborohydride, and lithium triethylborohydride.

The amount of such reducing agents that is used relative to the dicarbonyl compound represented by formula (7) is normally from 0.5 equivalents to 10.0 equivalents, preferably from 0.5 equivalents to 2.0 equivalents, and more preferably from 0.5 equivalents to 1.0 equivalents.

In a catalytic hydrogen reduction reaction, the solvent that is used can be selected from a wide range of commonly known solvents that are inert with respect to the reaction. Examples of solvents that can be used include alcohol solvents such as methanol, ethanol, n-propanol, isopropyl alcohol, and n-butanol; organic acids such as acetic acid and propionic acid; hydrocarbon solvents such as cyclohexane; and ether solvents such as tetrahydrofuran. One of these solvents may be used individually, or a mixture of two or more of these solvents may be used as necessary.

The amount of such solvents that is used relative to 1 part by mass of the diimino compound represented by formula (2) is normally approximately 1 part by mass to 500 parts by mass and preferably approximately 1 part by mass to 20 parts by mass.

Examples of metal catalysts that can be used in the catalytic hydrogen reduction reaction include palladium on carbon, platinum black (platinum on carbon), sulfided platinum on carbon, platinum oxide, Raney nickel, and Raney cobalt.

The amount of such metal catalysts that is used relative to the diimino compound represented by formula (2) is normally from 0.0001 parts by mass to 0.5 parts by mass, preferably from 0.0001 parts by mass to 0.1 parts by mass, and more preferably from 0.0001 parts by mass to 0.01 parts by mass.

The reaction can normally be carried out in a temperature range of from −78° C. to the boiling temperature of the solvent that is used. However, the reaction is normally carried out at approximately −10° C. to 50° C. and preferably at around room temperature.

The reaction is carried out under a hydrogen atmosphere at a pressure that is normally from atmospheric pressure to 10 MPa, preferably from atmospheric pressure to 1.0 MPa, and more preferably around atmospheric pressure.

Although it is not possible to make generalizations about the reaction time since the reaction time varies depending on the reaction temperature and so forth, the reaction is normally completed in approximately 0.5 hours to 24 hours.

In a situation in which the amine compound represented by formula (I) is used as an anti-aging agent, the blending amount of the amine compound relative to 100 parts by mass of the rubber component is preferably in a range of from 0.2 parts by mass to 10 parts by mass and more preferably in a range of from 0.5 parts by mass to 7.5 parts by mass. As a result of the blending amount of the amine compound represented by formula (I) being at least 0.2 parts by mass relative to 100 parts by mass of the rubber component, weather resistance of the rubber composition, such as ozone resistance, can be sufficiently improved and surface discoloration of a rubber article can be effectively inhibited. On the other hand, it is advantageous in terms of raw material costs of the rubber composition for the blending amount of the amine compound represented by formula (I) to be no greater than 10 parts by mass relative to 100 parts by mass of the rubber component since this enables the amount of the amine compound represented by formula (I) that is consumed as the anti-aging agent to be restricted while sufficiently improving weather resistance and inhibiting discoloration.

It should be noted that the presently disclosed rubber composition may contain the amine compound represented by formula (I) in combination with another anti-aging agent such as an amine-based anti-aging agent. In such a situation, the blending amount of the anti-aging agent other than the amine compound represented by formula (I) is preferably in a range of from 0 parts by mass to 5 parts by mass relative to 100 parts by mass of the rubber component.

<<Other Components>>

The presently disclosed rubber composition may contain carbon black, silica, or the like as a reinforcing filler. No specific limitations are placed on the carbon black that is used. Likewise, the silica can be any commercially available silica, among which, wet silica, dry silica, and colloidal silica are preferable, and wet silica is more preferable. The blending amount of the reinforcing filler is preferably in a range of from 5 parts by mass to 200 parts by mass relative to 100 parts by mass of the rubber component. In a situation in which silica is used as a reinforcing filler, it is preferable that a silane coupling agent is contained in an amount of approximately 1 mass % to 20 mass % relative to the silica from a viewpoint of reinforcing properties and it is more preferable that the silane coupling agent is contained in a range of from 6 mass % to 12 mass % from a viewpoint of heat-generation properties.

The presently disclosed rubber composition may further contain compounding agents commonly used in the rubber industry that are appropriately selected so as not to impair the objectives of the present disclosure. Examples of such compounding agents include vulcanizing agents, vulcanization accelerators, anti-scorch agents, softeners, zinc oxide, and stearic acid. Commercially available products may be suitably used as the compounding agents. The rubber composition can be produced by kneading, warming, extrusion, and the like of the rubber component, the amine compound represented by formula (I), and various compounding agents that are appropriately selected as necessary.

<Tire>

A presently disclosed tire includes at least one tire member in which the above-described rubber composition is used. A tread and a sidewall that are exposed at the outer surface are preferable examples of the aforementioned tire member. Through use of the above-described rubber composition, the presently disclosed tire benefits from superior weather resistance and inhibition of rubber article surface discoloration.

EXAMPLES

The following provides a more detailed explanation of the present disclosure through examples and production examples. However, the present disclosure is not in any way limited by the following examples.

Production Example 1

Production of N,N'-bis[4-(isopropylamino)phenyl]hexane-1,6-diamine (compound I-1)

(1) Production of N,N'-bis(4-nitrophenyl)adipamide

A suspension of 50 g of adipic acid in 50 mL of chloroform was prepared and 163 g of thionyl chloride was added thereto. Thereafter, a drop of N,N-dimethylformamide was further added to the suspension and the suspension was heated under reflux overnight. Next, chloroform and excess thionyl chloride were distilled by heating under normal pressure to yield a residue that was subsequently dissolved through addition of 30 mL of dehydrated tetrahydrofuran.

The resultant solution was dripped into an ice-cooled solution of 94.4 g of 4-nitroaniline, 64.9 g of pyridine, and 500 mL of dehydrated tetrahydrofuran. After stirring had been performed at room temperature for 2 days, water and diisopropyl ether were added to the resultant reaction liquid. The reaction liquid was filtered to obtain crystals that were then washed with water, diisopropyl ether, and ethyl acetate in this order, and were dried under reduced pressure to yield 126.5 g (96% yield) of N,N'-bis(4-nitrophenyl)adipamide as a yellow solid.

(2) Production of N,N'-bis(4-aminophenyl)adipamide

After 1.5 g of 5% palladium on carbon had been added to a suspension of 20 g of N,N'-bis(4-nitrophenyl)adipamide, 200 mL of methanol, and 300 mL of N,N-dimethylformamide, the system was purged with hydrogen gas and stirring was performed overnight at room temperature. Thereafter, 90 mL of N,N-dimethylformamide and 1.15 g of 5% palladium on carbon were added to the resultant reaction liquid and the reaction liquid was then stirred overnight under a hydrogen atmosphere. The reaction liquid was then filtered and the resultant filtrate was stirred overnight after water had been added thereto. The filtrate was filtered to obtain a solid that was then washed with a mixed liquid of water and methanol and dried under reduced pressure to yield 13.9 g (83% yield) of N,N'-bis(4-aminophenyl)adipamide as a gray solid.

(3) Production of N,N'-bis[4-(isopropylamino)phenyl]adipamide

After 12.8 g of acetone had been added to a solution of 24.0 g of N,N'-bis(4-aminophenyl)adipamide, produced according to the description in section (2), in 200 mL of methanol, the solution was ice-cooled and 20.3 g of sodium cyanoborohydride was added thereto. The resultant reaction liquid was adjusted to a pH of 6.5-7.5 using acetic acid and was stirred overnight at room temperature. Thereafter, 4 g of acetone was added and heating under reflux was performed overnight. The reaction liquid was stirred with 400 mL of water for 1 hour and was then filtered to obtain a solid. The solid was washed with water and dried under reduced pressure to yield 29.2 g (97% yield) of N,N'-bis[4-(isopropylamino)phenyl]adipamide as a dark brown solid.

(4) Production of N,N'-bis[4-(isopropylamino)phenyl]hexane-1,6-diamine (compound I-1)

A suspension of 16.3 g of lithium aluminum hydride in 300 mL of dehydrated tetrahydrofuran was prepared and 29.2 g of N,N'-bis[4-(isopropylamino)phenyl]adipamide was added thereto under ice cooling. The suspension was returned to room temperature and was stirred for 1 hour before being heated under reflux overnight. The resultant reaction liquid was ice cooled and was quenched with 30.8 mL of water. Thereafter, 30 mL of 1N sodium hydroxide aqueous solution and 30 mL of water were added and stirring was performed to produce a slurry that was subsequently filtered using Celite. Chloroform was added to the filtrate and liquid separation was performed to obtain an organic layer. The organic layer was dried using anhydrous magnesium sulfate and was subsequently concentrated under reduced pressure to obtain a solid residue. The solid residue was washed with hexane, diisopropyl ether, and ethyl acetate in this order, and was dried under reduced pressure to yield 20.3 g (75% yield) of N,N'-bis[4-(isopropylamino)phenyl]hexane-1,6-diamine (compound I-1) represented by the following formula.

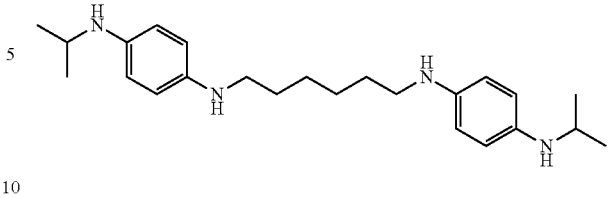

(I-1)

Properties: Dark brown solid
Melting point: 101.5° C.
$^1$H-NMR (300 MHz, DMSO-$D_6$, δ ppm): 1.05 (d, 12H), 1.35 (m, 4H), 1.49 (m, 4H), 2.87 (m, 4H), 3.35 (m, 2H), 4.28 (br-s, 2H), 4.58 (br-s, 2H), 6.39 (s, 8H)

Production Example 2

Production of N,N'-bis(4-anilinophenyl)hexane-1,6-diamine (compound 1-2)

(1) Production of N,N'-bis(4-anilinophenyl)adipamide

After 11.4 g of pyridine had been added to a solution of 24.1 g of N-phenyl-p-phenylenediamine in 250 mL of toluene, the solution was ice cooled and 12.0 g of adipoyl chloride was added thereto by dripping. The solution was stirred for 16 hours at 40° C. and the resultant reaction liquid was filtered after 200 mL of water had been added thereto. The filtered-off solid was crushed and washed with ethanol, and was dried under reduced pressure to yield 15.9 g (51% yield) of N,N'-bis(4-anilinophenyl)adipamide as a gray-white solid.

(2) Production of N,N'-bis(4-anilinophenyl)hexane-1,6-diamine (compound 1-2)

A suspension of 13.7 g of lithium aluminum hydride in 700 mL of dehydrated tetrahydrofuran was prepared and 25.0 g of N,N'-bis(4-anilinophenyl)adipamide, produced according to the description in section (1), was added thereto under ice cooling. Next, the suspension was returned to room temperature and stirred for 1 hour before being heated under reflux overnight. The resultant reaction liquid was ice cooled and was quenched with 300 mL of water. Thereafter, 50 mL of 1N sodium hydroxide aqueous solution and 200 mL of water were added and stirring was performed to produce a slurry that was subsequently filtered using Celite. Ethyl acetate was added to the filtrate and liquid separation was performed to obtain an organic layer. The organic layer was dried using anhydrous magnesium sulfate and was subsequently concentrated under reduced pressure. The resultant solid residue was washed with hexane/ethyl acetate (1:1) and was dried under reduced pressure to yield 19.9 g (85% yield) of N,N'-bis(4-anilinophenyl)hexane-1,6-diamine (compound 1-2) represented by the following formula.

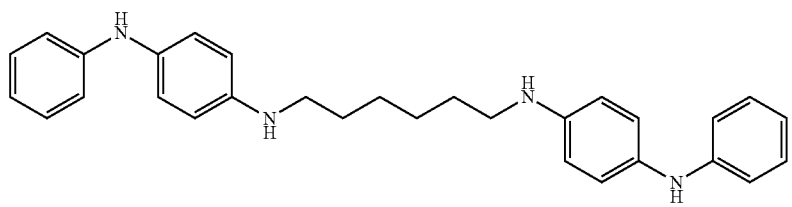

(I-2)

Properties: White solid
Melting point: 152° C.
¹H-NMR (300 MHz, DMSO-D$_6$, δ ppm): 1.34 (m, 4H), 1.54 (m, 4H), 2.96 (dt, 4H), 5.23 (t, 2H), 6.52 (d, 4H), 6.58 (dd, 2H), 6.76 (d, 4H), 6.87 (d, 4H), 7.07 (dd, 4H), 7.45 (s, 2H)

Production Example 3

Production of N,N'-bis[4-(heptan-4-ylamino)phenyl]decane-1,10-diamine (compound 1-3)

(1) Production of N,N'-bis(4-nitrophenyl)decanediamide

A suspension of 50 g of sebacic acid in 353 mL of chloroform was prepared and 118 g of thionyl chloride was added thereto. Thereafter, a drop of N,N-dimethylformamide was further added and heating under reflux was performed for 3 hours. Next, chloroform and excess thionyl chloride were distilled by heating under reduced pressure. The resultant residue was dripped into a solution of 68.3 g of 4-nitroaniline, 43.6 g of pyridine, and 500 mL of dehydrated tetrahydrofuran under ice cooling. The solution was returned to room temperature and was stirred for 1 day. Thereafter, 300 mL of water and 150 mL of methanol were added to the resultant reaction liquid and the reaction liquid was filtered. The filtered-off crystals were crushed and washed with water and methanol in this order, and were then dried under reduced pressure to yield 63.2 g (58% yield) of N,N'-bis(4-nitrophenyl)decanediamide as a yellow solid.

(2) Production of N,N'-bis(4-aminophenyl)decanediamide

After 2.25 g of 5% palladium on carbon had been added to a suspension of 30 g of N,N'-bis(4-nitrophenyl)decanediamide, 400 mL of methanol, and 400 mL of N,N-dimethylformamide, the system was purged with hydrogen gas and stirring was performed for 4 days at room temperature. Methanol was distilled from the resultant reaction liquid under reduced pressure. Thereafter, the reaction liquid was heated to 60° C. and was filtered. After 1,000 mL of water had been added to the filtrate, the filtrate was stirred overnight. Precipitated solid was filtered off, washed with water and ethanol in this order, and subsequently dried under reduced pressure to yield 24.4 g (94% yield) of N,N'-bis(4-aminophenyl)decanediamide as a gray solid.

(3) Production of N,N'-bis[4-(heptan-4-ylamino)phenyl]decanediamide

After 382.5 g of 4-heptanone had been added to a solution of 30.0 g of N,N'-bis(4-aminophenyl)decanediamide, produced according to the description in section (2), in 700 mL of methanol, the solution was ice cooled and 21.7 g of sodium cyanoborohydride was further added thereto. The solution was adjusted to a pH of 6.5-7.5 using acetic acid and was stirred for 10 days at 60° C. The resultant reaction liquid was stirred for a further 1 hour with 700 mL of water and was then filtered to obtain a solid. The solid was washed with water and isopropyl ether in this order, and was then dried under reduced pressure to yield 44.7 g (96% yield) of N,N'-bis[4-(heptan-4-ylamino)phenyl]decanediamide as a dark brown solid.

(4) Production of N,N'-bis[4-(heptan-4-ylamino)phenyl]decane-1,10-diamine (compound 1-3)

A suspension of 9.2 g of lithium aluminum hydride in 500 mL of dehydrated tetrahydrofuran was prepared and, after 20 g of N,N'-bis[4-(heptan-4-ylamino)phenyl]decanediamide had been added thereto under ice cooling, was heated under reflux for 5 hours. The resultant reaction liquid was ice cooled and was stirred with 300 mL of 10% sodium hydroxide aqueous solution to produce a slurry that was subsequently filtered using Celite. Next, 150 mL of chloroform was added to the filtrate and liquid separation was performed to obtain an organic layer. The organic layer was washed three times with 200 mL of water, was dried using anhydrous magnesium sulfate, and was subsequently concentrated under reduced pressure. The resultant solid residue was washed with hexane and dried under reduced pressure to yield 18.7 g (94% yield) of N,N'-bis[4-(heptan-4-ylamino)phenyl]decane-1,10-diamine (compound 1-3) represented by the following formula.

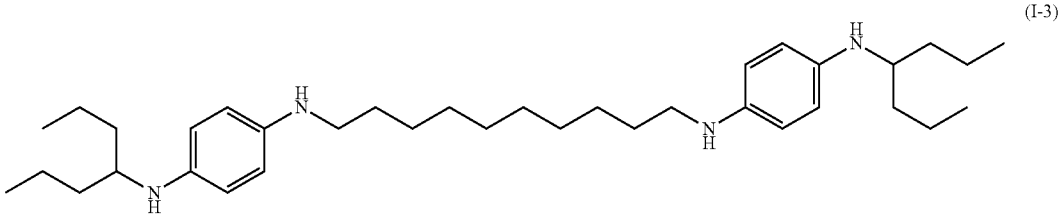 [SMILES: CCCC(CCC)Nc1ccc(NCCCCCCCCCCNc2ccc(NC(CCC)CCC)cc2)cc1]

(I-3)

Properties: Dark brown solid
Melting point: 62° C.
¹H-NMR (500 MHz, DMSO-D$_6$, δ ppm): 0.84 (m, 12H), 1.39 (m, 32H), 2.86 (br-s, 4H), 3.10 (br-s, 2H), 4.21 (d, 2H), 4.5 (br-s, 2H), 6.38 (m, 8H)

Production Example 4

Production of N,N'-bis(4-benzylaminophenyl)decane-1,10-diamine (compound 1-4)

(1) Production of N,N'-bis[4-(benzamide)phenyl]decanediamide

After 9.24 g of pyridine and 300 mL of dehydrated tetrahydrofuran had been added to 15 g of N,N'-bis(4-aminophenyl)decanediamide, 12.13 g of benzoyl chloride was further added by dripping under ice cooling. Stirring was performed for 3 days at room temperature and the resultant reaction liquid was filtered to obtain a solid. The solid was washed with methanol and water in this order, and was then crushed and washed with 300 mL of methanol. The washed solid was dried under reduced pressure to yield 22.7 g (98% yield) of N,N'-bis[4-(benzamide)phenyl]decanediamide as a brown solid.

(2) Production of N,N'-bis(4-benzylaminophenyl)decane-1,10-diamine (compound 1-4)

A suspension of 25 g of lithium aluminum hydride in 500 mL of dehydrated tetrahydrofuran was prepared and, after 25 g of N,N'-bis[4-(benzamide)phenyl]decanediamide, produced according to the description in section (1), had been added thereto under ice cooling, the suspension was heated under reflux for 1 day. The resultant reaction liquid was ice cooled and was stirred with 300 mL of 10% sodium hydroxide aqueous solution to produce a slurry that was subsequently filtered using Celite. After an aqueous layer had been separated by liquid separation, solvent was distilled under reduced pressure, and the resultant residue was dissolved through addition of 150 mL of chloroform and was then washed three times with 200 mL of water. The resultant organic layer was dried using anhydrous magnesium sulfate and was subsequently concentrated under reduced pressure to obtain a solid. The solid was washed with hexane and dried under reduced pressure to yield 21.6 g (96% yield) of N,N'-bis(4-benzylaminophenyl)decane-1,10-diamine (compound 1-4) represented by the following formula.

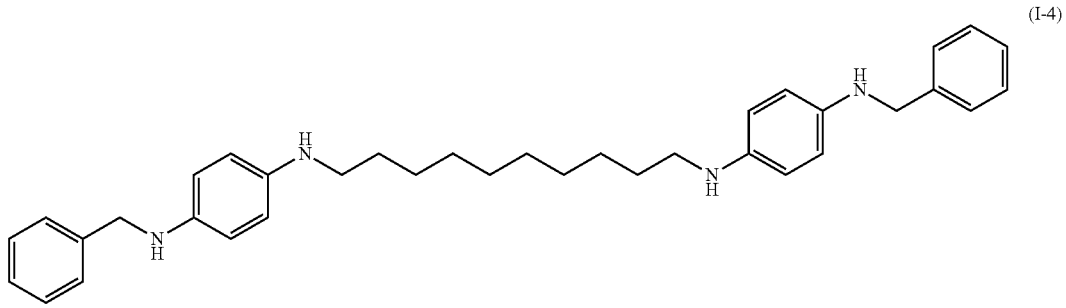 [SMILES: c1ccc(CNc2ccc(NCCCCCCCCCCNc3ccc(NCc4ccccc4)cc3)cc2)cc1]

(I-4)

Properties: Brown solid
Melting point: 111° C.
$^1$H-NMR (500 MHz, DMSO-D$_6$, δ ppm): 1.25 (m, 12H), 1.46 (m, 4H), 2.84 (br-s, 4H), 4.14 (d, 4H), 4.57 (m, 2H), 5.32 (m, 2H), 6.36 (d, 4H), 6.42 (d, 4H), 7.20 (m, 2H), 7.29 (m, 4H), 7.34 (m, 4H)

Production Example 5

Production of N,N'-bis(4-anilinophenyl)dodecane-2,11-diamine (compound 1-5)

(1) Production of 2,11-dodecanedione

First, 300 g of dibromohexane and 573 g of methyl acetoacetate were dissolved in 500 mL of dioxane. Next, 681 g of potassium carbonate was added, heating was performed to a temperature of from 80° C. to 85° C. (due to heat generation during the heating, the temperature increased to 100° C. and water cooling was then performed), and stirring was carried out at this temperature for 3 days. After returning the temperature to room temperature, an inorganic salt was removed by filtration and dioxane was distilled under reduced pressure. Next, the resultant residue was stirred for 17 hours at 60° C. with 2,400 g of 10% sodium hydroxide aqueous solution. The resultant reaction liquid was filtered after being returned to room temperature. Crystals that precipitated from the filtrate were filtered off and were dried under reduced pressure to yield 155.3 g (64% yield) of 2,11-dodecanedione.

(2) Production of N,N'-bis(4-anilinophenyl)dodecane-2,11-diamine (compound 1-5)

After 160 g of 2,11-dodecanedione, produced according to the description in section (1), 312 g of N-phenyl-p-phenylenediamine, and 111 g of sodium cyanoborohydride had been added to 2,000 mL of methanol, acetic acid was used to adjust the pH to 6.5-7.5 and stirring was performed for 4 days. The resultant reaction liquid was ice cooled and was filtered as a slurry to obtain a solid that was subsequently crushed and washed with 1,000 mL of water. The resultant solid was washed with 200 mL of cold methanol, further washed with 600 mL of cold methanol, and dried under reduced pressure to yield 347 g (80% yield) of N,N'-bis(4-anilinophenyl)dodecane-2,11-diamine (compound 1-5) represented by the following formula.

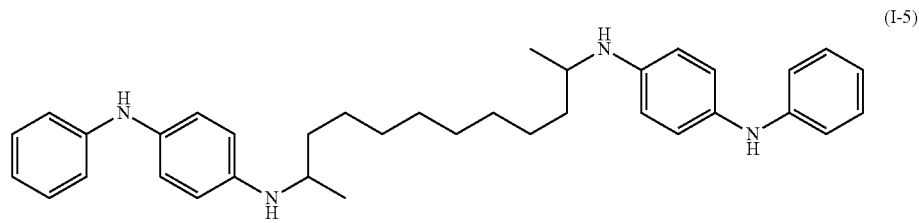 [SMILES: CC(CCCCCCCCC(C)Nc1ccc(Nc2ccccc2)cc1)Nc1ccc(Nc2ccccc2)cc1]

(I-5)

Properties: Purple solid
Melting point: 92° C.
$^1$H-NMR (300 MHz, DMSO-D$_6$, δ ppm): 1.07 (br-d, 6H), 1.26-1.36 (m, 14H), 1.46-1.53 (m, 2H), 3.29 (m, 2H), 4.98 (br-d, 2H), 6.51 (m, 4H), 6.59 (m, 2H), 6.77 (m, 4H), 6.86 (m, 4H), 7.08 (m, 4H), 7.44 (br-s, 2H)

Production Example 6

Production of N,N'-bis(4-anilinophenyl)hexadecane-2,15-diamine (compound 1-6)

(1) Production of 2,15-hexadecanedione

After 69.6 g of methyl acetoacetate and 63.6 g of potassium carbonate had been added to 45.0 g of dibromodecane, heating was performed to a temperature of from 80° C. to 85° C. (even after heating was stopped, the internal temperature increased temporarily to 110° C. due to heat of reaction), and stirring was performed at this temperature for 16 hours. The resultant reaction liquid was returned to room temperature and, after 50 mL of water and 240 g of 24% sodium hydroxide aqueous solution had been added thereto, was stirred for 16 hours at 60° C. The reaction liquid was then returned to room temperature before being filtered to obtain a solid. The solid was crushed and washed with 200 mL of water, and was dried under reduced pressure to yield 26.8 g (70% yield) of 2,15-hexadecanedione.

(2) Production of N,N'-bis(4-anilinophenyl)hexadecane-2,15-diamine (compound 1-6)

After 254 g of 2,15-hexadecanedione, produced according to the description in section (1), and 404 g of N-phenyl-p-phenylenediamine had been added to 3,800 mL of methanol and dissolved therein, 138 g of sodium cyanoborohydride was gradually added to the resultant solution. Thereafter, the solution was adjusted to a pH of 6.5-7.5 using acetic acid and was then stirred for 2 days. The resultant reaction liquid was ice cooled and adjusted to a pH of 9.6 using 25% sodium hydroxide aqueous solution before being filtered. The filtered-off solid was crushed and washed with 300 mL of cold methanol, and was then washed with 3,000 mL of water, 1,000 mL of water. and 2,000 mL of methanol in this order. The solid was subsequently crushed and washed with methanol, and was dried under reduced pressure to yield 440 g (75% yield) of N,N'-bis(4-anilinophenyl)hexadecane-2,15-diamine (compound 1-6) represented by the following formula.

(I-6)

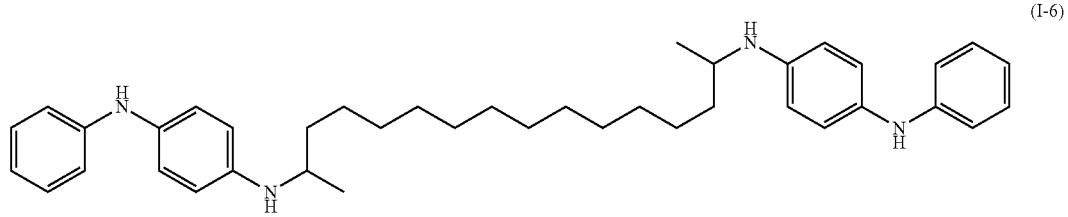 [SMILES: CC(CCCCCCCCCCCCC(C)Nc1ccc(Nc2ccccc2)cc1)Nc1ccc(Nc2ccccc2)cc1]

Properties: Pale purple solid
Melting point: 69° C.
$^1$H-NMR (300 MHz, CDCl$_3$, δ ppm): 1.17 (br-d, 6H), 1.2-1.7 (m, 24H), 3.41 (br-s, 2H), 5.36 (br-s, 2H), 6.56 (m, 4H), 6.76 (m, 2H), 6.82 (m, 4H), 6.99 (m, 4H), 7.17 (m, 4H), NH not detected.

Compounds 1-7 to 1-15 shown below in Table 1 were each produced in accordance with a method described in one of the above production examples. The Physico-chemical properties of these compounds are shown in Table 2.

TABLE 1

| Compound number | Compound |
|---|---|
| I-7 | |
| I-8 | |

TABLE 1-continued

| Compound number | Compound |
|---|---|
| I-9 | |
| I-10 | |
| I-11 | |
| I-12 | |
| I-13 | |
| I-14 | |
| I-15 | |

TABLE 2

| Number | Properties | $^1$H-NMR data |
|---|---|---|
| I-7 | Brown solid<br>Melting point 88° C. | $^1$H-NMR (500 MHz, DMSO-D$_6$, δ ppm): 0.85 (d, 6H), 0.88 (d, 6H), 1.00 (d, 6H), 1.15 (m, 2H), 1.33 (m, 14H), 1.50 (m, 4H), 1.70 (m, 2H), 2.87 (br-s, 4H), 3.31 (br-s, 2H), 4.20 (br-s, 2H), 4.55 (br-s, 2H), 6.39 (s, 8H) |
| I-8 | White solid<br>Melting point 130° C. | $^1$H-NMR (300 MHz, DMSO-D$_6$, δ ppm): 1.28 (m, 12H), 1.52 (m, 4H), 2.94 (dt, 4H), 5.21 (t, 2H), 6.51 (d, 4H), 6.58 (dd, 2H), 6.75 (d, 4H), 6.86 (d, 4H), 7.07 (dd, 4H), 7.47 (s, 2H) |
| I-9 | Pale purple solid<br>Melting point 74° C. | $^1$H-NMR (300 MHz, CDCl$_3$, δ ppm): 1.17 (d, 6H), 1.27 (m, 12H), 1.38 (m, 4H), 1.54 (m, 4H), 3.41 (m, 2H), 5.36 (m, 2H), 6.55 (d, 4H), 6.76 (dd, 2H), 6.82 (d, 4H), 6.98 (d, 4H), 7.17 (dd, 4H) |
| I-10 | Pale purple solid<br>Melting point 60° C. | $^1$H-NMR (300 MHz, CDCl$_3$, δ ppm): 1.17 (d, 6H), 1.25 (m, 20H), 1.38 (m, 4H), 1.56 (m, 4H), 3.40 (m, 2H), 5.36 (m, 2H), 6.56 (d, 4H), 6.76 (dd, 2H), 6.82 (d, 4H), 6.99 (d, 4H), 7.17 (dd, 4H) |
| I-11 | Gray-white solid<br>Melting point 128° C. | $^1$H-NMR (300 MHz, DMSO-D$_6$, δ ppm): 1.22 (m, 32H), 1.49 (m, 4H), 2.93 (m, 4H), 5.21 (m, 2H), 6.55 (m, 6H), 6.75 (d, 4H), 6.86 (d, 4H), 7.06 (dd, 4H), 7.44 (s, 2H) |
| I-12 | Yellow solid<br>Melting point 53° C. | $^1$H-NMR (300 MHz, DMSO-D$_6$, δ ppm): 0.99 (d, 12H), 1.76 (m, 2H), 2.69 (dd, 4H), 4.11 (d, 4H), 4.67 (br-t, 2H), 5.27 (br-t, 2H), 6.40 (m, 8H), 7.20 (m, 3H), 7.34 (m, 1H) |
| I-13 | Black oil | $^1$H-NMR (300 MHz, DMSO-D$_6$, δ ppm): 0.86 (t, 6H), 1.01 (d, 6H), 1.32 (m, 2H), 1.47 (m, 2H), 3.13 (m, 2H), 4.12 (br-d, 4H), 4.31 (br-d, 2H), 5.27 (br-t, 2H), 6.37 (m, 4H), 6.42 (m, 4H), 7.20 (m, 3H), 7.35 (m, 1H) |
| I-14 | Beige solid<br>Melting point 147° C. | $^1$H-NMR (300 MHz, DMSO-D$_6$, δ ppm): 0.90 (d, 12H), 1.76 (m, 2H), 2.69 (dd, 4H), 4.11 (d, 4H), 4.68 (br-t, 2H), 5.28 (br-t, 2H), 6.30 (d, 4H), 6.42 (d, 4H), 7.27 (s, 4H) |
| I-15 | Yellow solid<br>Melting point 94° C. | $^1$H-NMR (300 MHz, DMSO-D$_6$, δ ppm): 0.86 (t, 6H), 1.02 (d, 6H), 1.32 (m, 2H), 1.47 (m, 2H), 3.13 (m, 2H), 4.11 (br-d, 4H), 4.32 (br-d, 2H), 5.28 (br-t, 2H), 6.37 (m, 4H), 6.42 (m, 4H), 7.28 (s, 4H) |

Rubber compositions were produced by a standard method according to formulations 1 and 2 shown in Table 3. However, note that the blending amounts of various amine compounds and anti-aging agents were changed depending on the example (refer to Tables 4 and 5 described further below). Formulation 1 is a formulation for a rubber composition that it is envisaged will be used in a tire tread and formulation 2 is a formulation for a rubber composition that it is envisaged will be used in a tire sidewall. Each of the produced rubber compositions was vulcanized by a standard method. Ozone resistance and discoloration of the resultant vulcanized rubber compositions were evaluated by the methods described further below.

TABLE 3

| | Formulations | |
|---|---|---|
| Type of component | Formulation 1<br>Parts by mass | Formulation 2<br>Parts by mass |
| SBR *1 | 100 | — |
| BR | — | 50 |
| Natural rubber | — | 50 |
| Carbon black A *2 | 25 | — |
| Carbon black B *3 | — | 50 |
| Silica *4 | 25 | — |
| Silane coupling agent *5 | 2 | — |
| Stearic acid | 2 | 2 |
| Wax *6 | 2 | 2 |
| Zinc oxide | 3 | 3 |
| Vulcanization accelerator DPG *7 | 1.0 | 0.3 |
| Vulcanization accelerator MBTS *8 | 1.0 | 0.3 |
| Vulcanization accelerator CBS *9 | 1.0 | 0.8 |
| Sulfur | 1.5 | 2.0 |
| Amine compound X *10 | Variable amount (refer to Tables 4 and 5) | |
| Amine compound Y *11 | Variable amount (refer to Tables 4 and 5) | |
| Amine compound Z *12 | Variable amount (refer to Tables 4 and 5) | |
| Amine compound A *13 | Variable amount (refer to Tables 4 and 5) | |

TABLE 3-continued

| | Formulations | |
|---|---|---|
| Type of component | Formulation 1 Parts by mass | Formulation 2 Parts by mass |
| Anti-aging agent 6PPD *14 | Variable amount (refer to Tables 4 and 5) | |
| Anti-aging agent TMQ *15 | Variable amount (refer to Tables 4 and 5) | |

*1 SBR: Styrene-butadiene copolymer rubber, #1500 produced by JSR Corporation
*2 Carbon black A: SEAST 7HM produced by Tokai Carbon Co., Ltd.
*3 Carbon black B: SEAST F produced by Tokai Carbon Co., Ltd.
*4 Silica: Nipsil VN3 produced by Tosoh Silica Corporation
*5 Silane coupling agent: Bis(3-ethoxysilylpropyl)tetrasulfide
*6 Wax: Microcrystalline wax, Ozoace 0701 produced by Nippon Seiro Co., Ltd.
*7 Vulcanization accelerator DPG: NOCCELER D produced by Ouchi Shinko Chemical Industrial Co., Ltd.
*8 Vulcanization accelerator MBTS: NOCCELER DM produced by Ouchi Shinko Chemical Industrial Co., Ltd.
*9 Vulcanization accelerator CBS: SANCELER CM-G produced by Sanshin Chemical Industry Co., Ltd.
*10 Amine compound X: Compound I-6 produced in Production Example 6
*11 Amine compound Y: Compound I-4 produced in Production Example 4
*12 Amine compound Z: Compound I-13
*13 Amine compound A: Compound represented by following formula

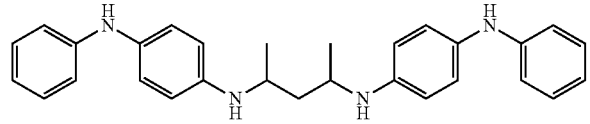 [SMILES: CC(CC(C)Nc1ccc(Nc2ccccc2)cc1)Nc1ccc(Nc2ccccc2)cc1]

*14 Anti-aging agent 6PPD: NOCRAC 6C produced by Ouchi Shinko Chemical Industrial Co., Ltd., N-phenyl-N'-(1,3-dimethylbutyl)-p-phenylenediamine
*15 Anti-aging agent TMQ: NONFLEX RD-S produced by Seiko-Chemical Co., Ltd., polymerized 2,2,4-trimethyl-1,2-dihydroquinoline <Ozone Resistance>

A test piece of each of the rubber compositions was subjected to an ozone degradation test in accordance with JIS K6301 under conditions of a temperature of 40° C., an ozone concentration of 50 pphm, and elongation of 20%. After 50 hours had passed, the state of degradation of the test piece was inspected and was evaluated using the following three-level scale based on the number of cracks that had formed.

A: Small number of cracks
B: Large number of cracks
C: Countless number of cracks Moreover, the test piece was evaluated using the following five-level scale based on the size and depth of cracks.

1: Cracks not visible by naked eye but visible under ×10 magnifying glass
2: Cracks visible by naked eye
3: Deep and relatively large cracks (less than 1 mm)
4: Deep and large cracks (at least 1 mm and less than 3 mm)
5: Cracks of at least 3 mm or severing likely to occur Note that in a situation in which cracks were not observed, an evaluation of "no cracks" was given. The results of this evaluation are shown in Tables 4 and 5.

<Discoloration>

After each of the test pieces had been subjected to the ozone degradation test described above, surface discoloration of the test piece was visually evaluated using the following four-level scale. The results of this evaluation are shown in Tables 4 and 5.

$A^+$: Black and glossy
$A^-$: Black but not glossy
$A^-$Surface discoloration confirmed
F: Discoloration of entire surface

TABLE 4

| | Example 1 | Example 2 | Example 3 | Example 4 | Example 5 | Example 6 | Example 7 | Example 8 | Example 9 | Example 10 | Example 11 |
|---|---|---|---|---|---|---|---|---|---|---|---|
| Formulation | 1 | 2 | 2 | 2 | 2 | 2 | 2 | 2 | 2 | 2 | 2 |
| Amine compound X | 1 | 0.2 | 1 | 3 | 6 | 10 | 3 | 1.5 | 1.5 | — | — |
| Amine compound Y | — | — | — | — | — | — | — | — | — | 3 | — |
| Amine compound Z | — | — | — | — | — | — | — | — | — | — | 3 |
| Amine compound A | — | — | — | — | — | — | — | — | — | — | — |
| Anti-aging agent 6PPD | — | — | — | — | — | — | — | 1.5 | 1.5 | — | — |
| Anti-aging agent TMQ | 0.3 | — | — | — | — | — | 1 | — | 1 | — | — |
| Ozone resistance | A-2 | B-4 | A-3 | No cracks | No cracks | No cracks | No cracks | No cracks | No cracks | A-2 | A-2 |
| Discoloration | $A^+$ | $A^+$ | $A^+$ | $A^+$ | A | $A^-$ | $A^+$ | A | A | A | A |

TABLE 5

| | Comparative Example 1 | Comparative Example 2 | Comparative Example 3 | Comparative Example 4 | Comparative Example 5 | Comparative Example 6 | Comparative Example 7 |
|---|---|---|---|---|---|---|---|
| Formulation | 1 | 2 | 2 | 2 | 2 | 2 | 2 |
| Amine compound X | — | — | — | — | — | — | — |
| Amine compound Y | — | — | — | — | — | — | — |
| Amine compound Z | — | — | — | — | — | — | — |
| Amine compound A | — | — | — | — | — | 3 | — |
| Anti-aging agent 6PPD | 1 | 1 | 3 | 6 | 10 | — | 3 |

TABLE 5-continued

| | Comparative Example 1 | Comparative Example 2 | Comparative Example 3 | Comparative Example 4 | Comparative Example 5 | Comparative Example 6 | Comparative Example 7 |
|---|---|---|---|---|---|---|---|
| Anti-aging agent TMQ | 0.3 | — | — | — | — | — | 1 |
| Ozone resistance | B-3 | B-4 | A-3 | A-2 | A-1 | A-1 | A-2 |
| Discoloration | A | A | A⁻ | F | F | F | A⁻ |

From Tables 4 and 5, it can be seen that in the case of rubber compositions that contained the amine compound represented by formula (I) blended with at least one rubber component selected from natural rubber and diene-based synthetic rubbers, and also in the case of rubber compositions according to the present disclosure that contained another anti-aging agent in combination with the amine compound represented by formula (I), weather resistance was improved and surface discoloration was inhibited compared to rubber compositions that only contained conventional anti-aging agents.

The invention claimed is:

1. An amine compound represented by formula (I) shown below

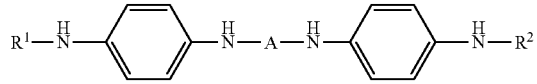
(I)

where, in formula (I), $R^1$ and $R^2$ each represent a phenyl group, A represents an alkylene group having a carbon number of 6-30, and A does not include an interposed phenylene group.

2. An anti-aging agent for natural rubber and diene-based synthetic rubber-use comprising the amine compound of claim 1.

3. A rubber composition comprising
at least one rubber component selected from natural rubber and diene-based synthetic rubbers and, blended therewith, at least one amine compound represented by formula (II) shown below

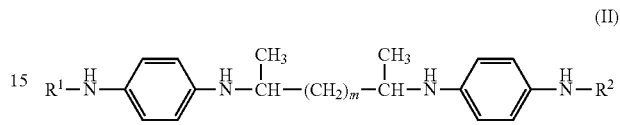
(II)

where, in formula (II), $R^1$ and $R^2$ each represent a phenyl group and m represents an integer of 8-16.

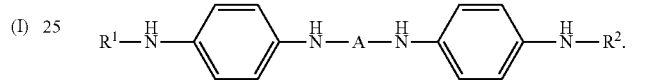
(I)

4. The rubber composition of claim 3, wherein
a blending amount of the at least one amine compound is in a range of from 0.2 parts by mass to 10 parts by mass relative to 100 parts by mass of the at least one rubber component.

5. A tire comprising a tire member comprising the rubber composition of claim 3.

6. The tire of claim 5, wherein
the tire member is either or both of a tread and a sidewall.

* * * * *

UNITED STATES PATENT AND TRADEMARK OFFICE
CERTIFICATE OF CORRECTION

PATENT NO. : 10,059,829 B2
APPLICATION NO. : 15/312785
DATED : August 28, 2018
INVENTOR(S) : Aya Saiki et al.

It is certified that error appears in the above-identified patent and that said Letters Patent is hereby corrected as shown below:

In the Specification

Column 14, Line 36, please delete "compound 1-2" and insert --compound I-2--.
Column 14, Line 55, please delete "compound 1-2" and insert --compound I-2--.
Column 15, Line 11, please delete "compound 1-3" and insert --compound I-3--.
Column 16, Line 17, please delete "compound 1-3" and insert --compound I-3--.
Column 16, Line 40, please delete "compound 1-4" and insert --compound I-4--.
Column 16, Line 55, please delete "compound 1-4" and insert --compound I-4--.
Column 18, Lines 2-3, please delete "compound 1-4" and insert --compound I-4--.
Column 18, Line 26, please delete "compound 1-5" and insert --compound I-5--.
Column 18, Line 45, please delete "compound 1-5" and insert --compound I-5--.
Column 18, Lines 56-57, please delete "compound 1-5" and insert --compound I-5--.
Column 19, Line 11, please delete "compound 1-6" and insert --compound I-6--.
Column 20, Line 6, please delete "compound 1-6" and insert --compound I-6--.
Column 20, Line 22, please delete "compound 1-6" and insert --compound I-6--.
Column 20, Line 42, please delete "compound 1-7 to 1-15" and insert --compound I-7 to I-15--.

In the Claims

Claim 3, Column 28, after Line 20, please delete "  ".

Signed and Sealed this
Sixteenth Day of April, 2019

Andrei Iancu
*Director of the United States Patent and Trademark Office*